United States Patent [19]
Lahille et al.

[11] Patent Number: 5,380,325
[45] Date of Patent: Jan. 10, 1995

[54] OSTEOSYNTHESIS DEVICE FOR SPINAL CONSOLIDATION

[75] Inventors: Michel Lahille, Vauhallan; Jean-Philippe Lemaire, Couternon; Sami Khalife, Amiens, all of France

[73] Assignee: Biomat, Igny, France

[21] Appl. No.: 147,532

[22] Filed: Nov. 5, 1993

[30] Foreign Application Priority Data

Nov. 6, 1992 [FR] France ............... 92 13414

[51] Int. Cl.⁶ .................................. A61B 17/56
[52] U.S. Cl. .................................. 606/61; 606/59; 606/73; 403/294; 403/399; 403/400
[58] Field of Search ............... 606/61, 59, 72, 73, 606/60, 53, 54; 403/294, 292, 400, 399, 396, 389

[56] References Cited

U.S. PATENT DOCUMENTS

| | | | |
|---|---|---|---|
| 312,580 | 2/1885 | O'Malley | 403/389 |
| 4,110,951 | 9/1978 | Padrun | 403/399 |
| 5,005,562 | 4/1991 | Cotrel | 606/61 |
| 5,222,954 | 6/1993 | Baker et al. | 606/61 |
| 5,300,073 | 4/1994 | Ray et al. | 606/61 |

Primary Examiner—Tamara L. Graysay
Attorney, Agent, or Firm—Laubscher & Laubscher

[57] ABSTRACT

A consolidation rod and plural members, such as pedicular screws and vertebral claws, have threaded sections extending from a head and fitted with a nut. A rigid fast connection between the rod and a member providing high adhesion is ensured by a fastener for clamping the rod owing to the screwing of the nut. The fastener comprises a first bore sliding on the rod, a slit opening into the first bore and narrowed by nut screwing, and a second bore passing through the slit and passed through by the threaded section. An indented plate, or a bar with threaded ends fitted with hooks transversely stabilizes two consolidation rods. A connector longitudinally stabilizes two consolidation rods.

20 Claims, 3 Drawing Sheets

OSTEOSYNTHESIS DEVICE FOR SPINAL CONSOLIDATION

BACKGROUND OF THE INVENTION

1. Field of the Invention

This invention relates to an osteosynthesis device comprising a rod, and a member having a threaded section extending from a head and fitted with a nut.

2. Description of the Prior Art

Such a known osteosynthesis device for stabilizing and correcting the spine is fitted with at least two screws, as a member with a threaded section. In addition to the threaded section serving to connect each of the screws to the consolidation rod by means of the nut, the screw comprises a partially or completely threaded portion to be implanted most often in the pedicle of a vertebra.

The consolidation rod extends along the spinous apophysis of the spine and must be connected quickly to the threaded sections of plural pedicular screws, while ensuring an accurate positioning of the screws in relation to one another and especially an efficient dismountable connection between the screws and the rod.

According to the prior art, the rod is connected to a screw by tightening the rod between two adequate nuts screwed onto the threaded screw section and laterally to the latter. According to another known embodiment, a portion of the rod is wedged between a washer having a half-gutter-shaped rim and a bevelled edge of the nut; the nut pushes the rod onto the washer and the washer against the screw head separating the threaded section and the implanted screw portion.

These known connections between screws and rod do not provide a sufficient bearing area for the nuts, or for the half-gutter-shaped washer and the nut, on the rod to prevent rotation, or even translation, of the rod. The threaded section and particularly the nuts undergo asymmetrical stresses about their axis, thereby increasing the risk of breakage of these parts, notably when the consolidation rod is subjected to a bending or twisting of the spine.

OBJECTS OF THE INVENTION

The main object of this invention is to remedy the preceding disadvantages according to the prior art.

Another object of this invention is to improve the rigidity and longevity of the connection between a consolidation rod and a pedicular screw, while guaranteeing speedy surgical assembly of this connection.

SUMMARY OF THE INVENTION

Accordingly, an osteosynthesis device comprises
a rod, a member having a threaded section extending from a head and fitted with a nut, and a connecting fastener,
the fastener comprising a first smooth bore passed through by the rod, a first slit opening axially into the first bore, and a second smooth bore substantially perpendicular to the first slit and passed through by a portion of the threaded member section located between the member head and the nut, and a second slit opening axially into the second bore and having a width greater than the diameter of the threaded member section.

The connecting fastener accommodated partially between the nut and the screw head offers a bearing area on the periphery of the rod that is incomparably greater than the known nuts or the known combination of the nut and half-gutter washer. By way of the clamping, the fastener can almost completely hem in a section of the rod and thus adhere to almost the entire periphery of the circular cross-section of the rods. The assembly is particularly rigid, notably against all attempted rotations of the rod about its axis.

When the first slit before assembling with the screw has a relatively small width, the nut tightening the arms of the fastener separed by the first slit is properly used so that the nut does not submit by forces close to radial directions.

So as to hold the threaded section of the screw in the connecting fastener when the nut is screwing onto the threaded section and narrowing the first slit, the nut comprises a cylindrical shank having a diameter that is substantially equal to the diameter of the second bore and more than the width of the second slit thereby penetrating into the second bore.

The second slit may be substantially perpendicular or parallel to the first bore, thereby facilitating the introduction of the fastener between the rod and the head of the screw particularly when the consolidation rod connects numerous screws and other members with threaded section.

According another embodiment, a member with threaded section may comprise a claw-shaped portion separated from the threaded section by the head.

The devide may comprise a means having a bore slidably passed through by the rod and having a claw-shaped portion, and a locking means radial to the rod for maintaining motionless the means slidably passed through by the rod.

The invention also relates to the transversal stabilization between two consolidation rods side by side, e.g. disposed to the right and to the left of the spinous apophysis, and the longitudinal stabilization between two rods along the same side of the spinous apophysis.

According to the invention, when a second consolidation rod extends laterally to the previously mentioned first rod, a first transversal stabilizing means comprises a plate extending transversal to the two rods and having a longitudinal slot, two hooks each having a threaded section passing through the plate slot and a holding portion partially surrounding one of the two rods, and two nuts respectively screwed onto threaded hook sections for tightening the plate against the two rods thereby confining the rods between the plate and the hook holding portions.

According to a second embodiment, a transversal stabilizing means comprises a bar extending transversal to the two rods, two hooks having hooking portions to be hooked to the two rods and means for quickly securing the hooks to ends of the bar.

According to the invention, a longitudinal stabilizing means connecting ends of two consolidation rods, e.g. between ends of the rods substantially aligned each with the other, comprises a connector having a longitudinal orifice with an oblong cross-section passed through by the two rods, and a means for spacing apart the two rods thereby blocking the rods in the orifice.

BRIEF DESCRIPTION OF THE DRAWINGS

Further features and advantages of the invention will be apparent from the following particular description of several preferred embodiments of this invention as illustrated in the corresponding accompanying drawings in which.

DESCRIPTION OF THE PREFERRED EMBODIMENTS

Figure 1:
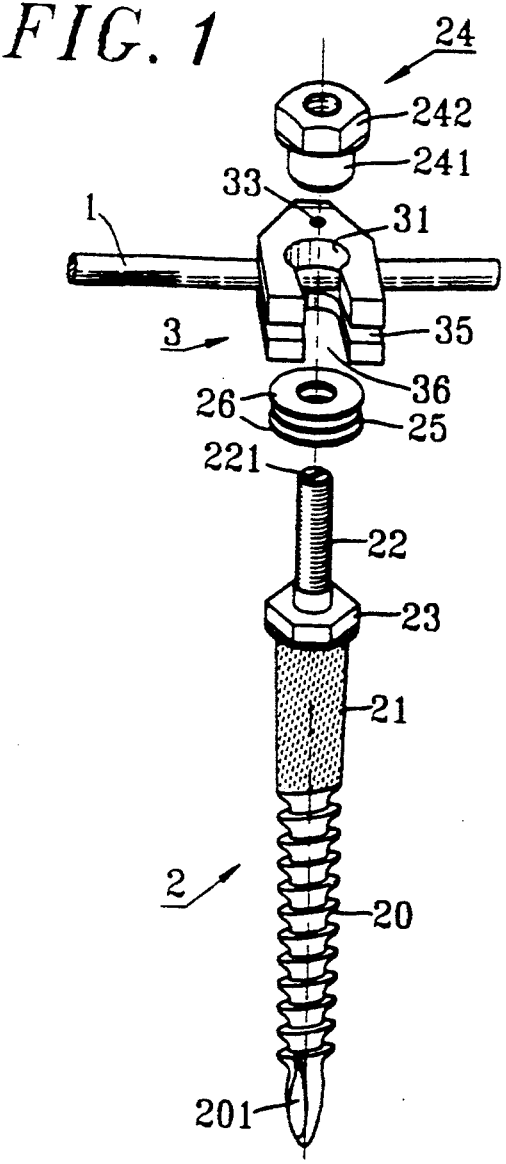
FIG. 1 is an exploded perspective view of a basic assembly of a pedicular screw and a consolidation rod in an osteosynthesis device embodying the invention.

An osteosynthesis device embodying the invention comprises at least one basic assembly for connecting a consolidation rod 1 to a member with a threaded section, which is constituted by a pedicular screw 2 according to FIG. 1, by means of a fast connecting means 3. These various members and others referred to hereinafter are essentially metallic, e.g. in a titanium-based alloy.

The pedicular screw 2 is stud-shaped and is comprised of a substantially tapered partially threaded portion 20-21, a cylindrical section 22 threaded substantially over its entire length, and an intermediate gripping head 23, in this instance of hexagonal cross-section, situated between the threaded portion and section.

The portion 20-21 comprises, substantially over half its length, a substantially tapered section 20 having a relatively large rounded thread pitch, terminated by a self-cutting end with a crimp-effect tip 201, i.e., a tip comprising two opposite axial grooves with a V cross-section, so as to easily penetrate and be intimately anchored into the spongy bone of a vertebral body. A tapered section 21 located between the section 20 and the head 23 completes the screw portion 20-21. The section 21 is covered with a coarse coating in pure porous titanium in order for its micro-anfractuousities to be filled in by bone growth of the vertebral pedicle in which it is implanted. This anchoring of the coarse section 21 in the pedicle ensures a primary stability of the device, unlike a fibrous connection with a known smooth screw section in nickel-chrome or cobalt-chrome running through the pedicle. The gripping head 23 is designed to be gripped by a corresponding handling key thereby screwing threaded section 20 into the pedicle and vertebral body until head 23 abuts against the cortical bone.

The second threaded section 22 of the screw 2 constitutes the posterior extra-vertebral end of the screw 2 after implantation of the screw, and is designed to cooperate with the connecting means 3 and to receive a nut 24. As shown at 22a in FIG. 6, this posterior threaded section 22 is initially designed relatively long so as to adapt its length by presurgical sawing. The end face of the threaded section 22 comprises a slit to accommodate a screwdriver, as illustrated in FIG. 1, or a polygonal e.g. hexagonal end for cooperating with a handling key so as to prevent any rotation of the screw 2 during tightening of a connecting means 3 by the nut 24, as will be seen hereinafter.

Figure 2:
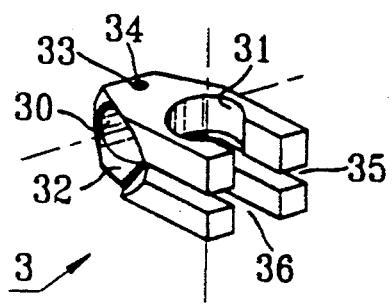
FIG. 2 is a perspective view of a first fastener for connecting a consolidation rod to a member with a threaded section such as a pedicular screw or first vertebral claw.

As shown in FIGS. 1 and 2, a fast connecting means is a fastener 3 substantially in the shape of a small block which is divided into anterior and posterior face sides symmetrical about a slit 35. First halves, trapezoidally bevelled in this instance, of the anterior and posterior sides of the fastener 3, which are substantially "vertical" after implantation of the device, are parallely drilled into a smooth bore 30 slidably receiving the rod 1. Second halves of the two other "anterior and posterior" sides of the fastener 3 are perpendicularly drilled at a second smooth bore 31 which is perpendicular to the first bore 30 and does not intersect the latter. The bore 31 has a cross-section contained in the polygonal sections of the head 242 of the nut 24 and of the head 23 of the screw 2. The threaded section 22 of a screw 2 notably is freely received in the bore 31.

The ends of the first bore 30 have countersinkings 32 facilitating the penetration of the rod 1 into the bore 30. On the posterior side of the fastener 3 is provided a small tapped hole 33 opening radially into the first smooth bore 30 in order for a small hexagonal socket headless locking screw 34 screwed into the hole 33 to maintain the fastener 3 motionless on the rod 1 in a temporarily desirable position.

Figure 6:
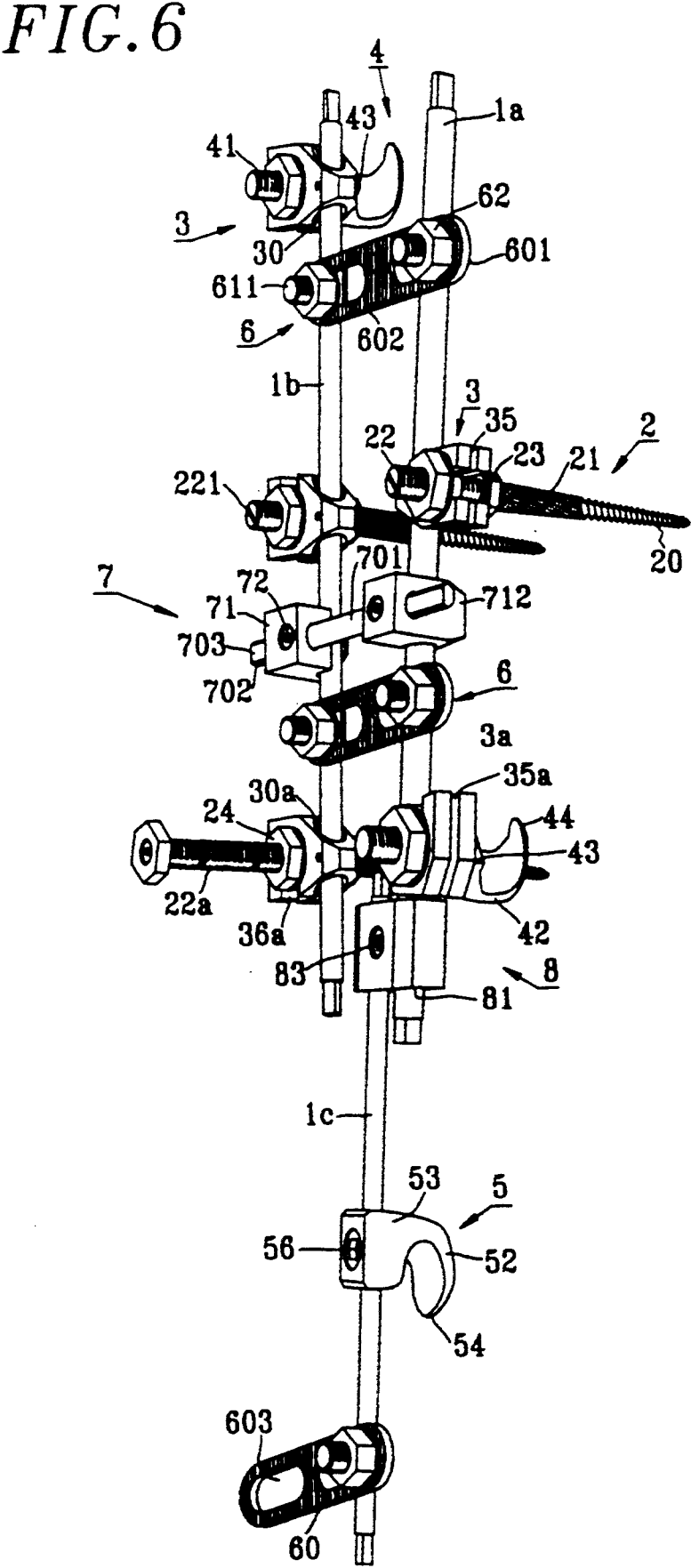
FIG. 6 is a schematic perspective view of an osteosynthesis device comprising plural consolidation rods connected together by transversal and longitudinal stabilizing means.

The fastener 3 also comprises two rectangular slits 35 and 36 which extend substantially perpendicular to one another from a "lateral" fastener side which is parallel to bore 30 and opposite bore 30 in relation to bore 31 and which is oriented substantially towards the left or right after implantation (FIG. 6). The first slit 35 is made along a substantially center plane of the fastener that is coplanar with the axis of the bore 30. The slit 35 is perpendicularly passed through by the bore 31, opens axially into the bore 30, and is of width considerably smaller than the diameter of the rod 1 and bore 30. The second slit 36 opens axially into the second bore 31, is substantially perpendicular to the first bore 30, and has a width greater than the diameter of the threaded screw section 22 and smaller than the diameter of the bore 31. The second bore 31 receives a complementary bevel-ended cylindrical shank 241 which is disposed under the polygonal head 242 of the nut 24. The shank 241 is shorter than the bore 31 and is of diameter substantially equal to the diameter of the second bore 31 and greater than the width of the second slit 36 so that the shank does not escape via the slit 36 after having tightened the nut 24.

However, according to another embodiment, the slit 36 can be suppressed.

The embodiment illustrated in FIG. 1 advantageously avoids lateral sliding of the fastener 3 in relation to the screw 2 during assembly thereof, by way of the confining of the shank 241 in the bore 31 which is wider than the slit 36, although the section 22 passes through slit 35 during assembly of the device.

It thus appears that the fastener 3 constitutes a collar clamping the rod 1 and connecting the rod 1 to the screw 2. The rod slides in the bore 30 during assembly and positioning of the different components of the osteosynthesis device and subsequent to implantation of the screw 2. The anterior and posterior sides of the fastener 3 are hemmed in between the screw head 23 and the nut head 242 so as to substantially bend said sides towards one another and to narrow the first slit 35 to block the rod 1 by clamping, and to simultaneously rapidly and solidly connect to the fastener 3 and therefore to the rod 1. By way of the low width of the first slit 35 of the fastener 3, the almost entire circular periphery of the section of the rod 1 contained in the bore 30 is clamped in the first bore 30 which, initially slit, closes itself and arches around the rod 1. This almost total clamping prevents any sliding of the fastener 3 along and/or about the rod 1, and thus endows a more extensive bearing area and a more rigid connection between the rod and the screw 2 by comparison with the prior art. During screwing of the nut 24 and narrowing of the slit 35, the screw 2 is maintained motionless, if the case arises, by the head 23 or the slit 221.

In addition, a release of the clamping of the rod 1 by the bore 30 in order to modify the relative positions of the screw 2 and rod 1 is obtained by slightly unscrewing the nut 24, while still maintaining the shank 241 in the bore 31 so that the threaded section 22 does not escape via the slit 36.

Figure 3:
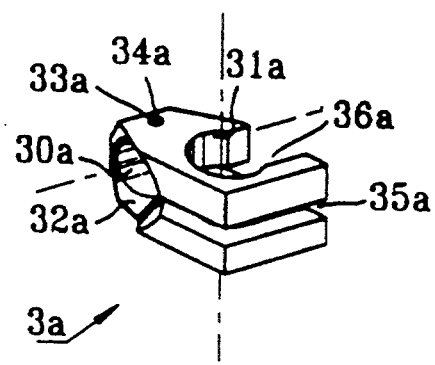
FIG. 3 is a perspective view of a second fastener for connecting a consolidation rod to a member with a threaded section.

According to another embodiment shown in FIG. 3, a connecting fastener 3a has, in a similar manner to the fastener 3 in FIG. 2, a first smooth bore 30a having a countersink 32a and into which opens a first slit 35a axial to this bore, a second smooth bore 31a perpendicular to the bore 30a, and a small tapped hole 33a for a locking screw 34a, radial to the bore 30. In the fastener 3a is provided a second slit 36a which, like the slit 36 in the first fastener 3, opens axially into the second bore 31 and is perpendicular to the first slit 35a, but which is made laterally in an "upper" or "lower" side of the fastener 3a substantially parallel, and not perpendicular, to the first bore 30a.

The invention thus provides two types of fasteners 3a with a lateral slit 36a, depending on whether the slit 36a is oriented "upwards" or "downwards" towards the coccyx, as shown in FIG. 6.

Figure 4:
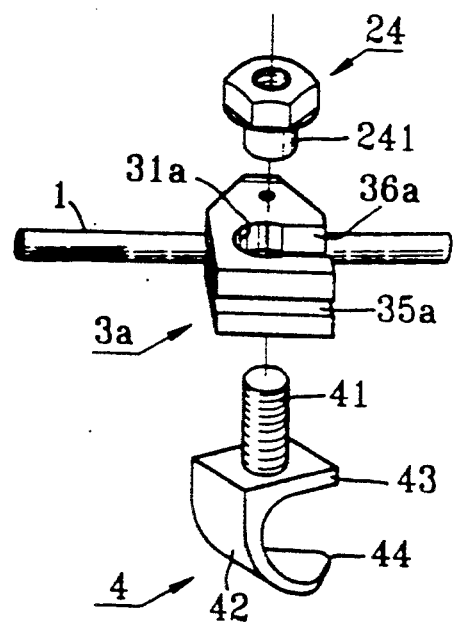
FIG. 4 is an exploded perspective view of another basic assembly of a consolidation rod and a vertebral claw with a threaded section in an osteosynthesis device embodying the invention.

These three types of fasteners, in conjunction with the slidable and rotatable mounting of the bore 30, 30a onto the rod 1, thus enable the threaded section 22 of a screw 2 (or that 41 of a vertebral claw 4; FIG. 4) to be approached from almost any direction. In particular, a selected one of these fasteners can connect a rod 1 to a screw, irrespective of the inclination of the rod in relation to the screw, in a plan substantially perpendicular to the screw. The small temporary locking screws 34, 34a assist in maintaining the corresponding fasteners 3, 3a in required positions along a common rod 1 when plural fasteners 3, 3a mounted on the rod 1 must be engaged simultaneously by the slits 36, 36a and the bores 31, 31a into threaded sections 22 of corresponding screws 2 (or threaded sections 41 of claws 4; FIG. 6).

The assembly of a rod 1, a member with a threaded section such screw 2 and a fastener 3, 3a preferably further comprises a means passed through by the threaded section 22 of the screw 2 and located between the screw head 23 and the nut head 242 in order to dampen relative micro-movements between the rod 1 and the screw 2. This damping means thus contributes to the cancelling of the spinal micro-movements from one vertebra to another and therefore from one pedicular screw to another and thus to avoiding cracks or breaks in the screw 2 and/or the rod 1. This damping means comprises a washer 25 in damping material, such as elastomer or polyurethane or silicon, slipped onto the threaded section 22. According to the embodiment illustrated in FIG. 1, this washer 25 is braced by two metal guiding washers 26, which are preferably thermobonded to the washer 25; this washer assembly 25+26 is slipped over the section 22 and hemmed in at the base of the section 22, between the screw head 23 and the anterior side of the fastener 3, or 3a.

According to other embodiments, this first washer assembly can only comprise one washer 25 in damping material and one single metal washer 26. A second washer assembly comprising at least one washer in damping material either replaces the first washer assembly, or is combined with the latter, and is disposed between the posterior side of the fastener 3, 3a and the head 242 of the nut 24.

In reference to FIG. 4, the member with the threaded section previously constituted by a screw 2 is, in this instance, in the form of a first vertebral claw 4. This claw 4 also comprises a cylindrical threaded section 41 intended to engage with a nut 24 and to penetrate into a second bore 31, 31a of the fastener 3, 3a via the second slit 36, 36a of this fastener; as an example, FIG. 4 shows an assembly of a claw 4 with a fastener 3a having a second lateral slit 36a. Underlying the threaded section 41 of the claw 4 is provided a substantially circular semi-crescent-shaped portion 42 forming a "claw" which is separated from the threaded portion 41 by a rectangular head 43 and which is terminated by a substantially pointed end 44. The portion 42 is intended to hook edges of various vertebral recesses, notably pedicular, lumbar, thoracic, supralaminar, sublaminar and transverse ones. As with the screw 2, the claw 4 can be approached substantially laterally, from the right or the left, from above or below, by one of the three fasteners 3, 3a, and its semi-crescent-shaped portion 42 can be oriented in any direction whatsoever by means of the rotation of the threaded portion 41 in the bore 31, 31a of the fastener 3, 3a.

Figure 5:
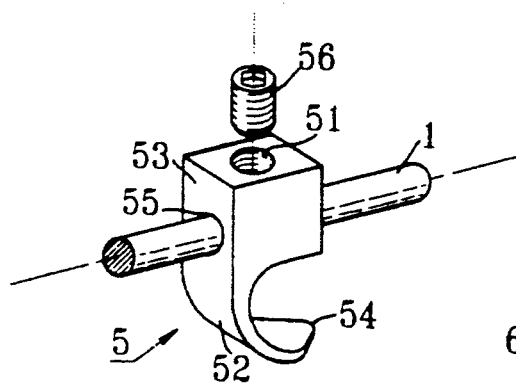
FIG. 5 is a partially exploded perspective view of a second vertebral claw mounted slidably on a consolidation rod.

A second claw 5 similar to the previous claw 4 is shown in FIG. 5. This second claw 5 comprises a semi-crescent-shaped portion 52 similar to the portion 42, and a parallelepiped head 53 comprising a bore 55 which is slidably mounted over a consolidation rod 1. According to the embodiment illustrated in FIG. 5, the tip 54 of the claw is situated in a plane axial to the bore 55; however, according to other embodiments, the semi-crescent-shaped portion 52 can be oriented in any way whatsoever and as a functions of requirements about a center axis of the head 53 perpendicular to the bore 55. Along this center axis is provided a hole 51 tapped from the often posterior side of the head 53 opposite the semi-crescent-shaped portion 52 and opening radially into the bore 55. A small hexagonal socket headless locking screw 56 penetrates into the hole 51 so as to block translation and rotation of the rod 1 in the bore 55, and to thus maintain the claw 5 on the rod 1. Such a second claw 5 mounted slidably on the rod 1 can be anchored e.g. in a transverse or spinous apophysis of a vertebra.

FIG. 6 schematically shows, by way of an example, a latero-posterior view of a rigid assembly of various parts susceptible of entering into the constitution of an osteosynthesis device for spinal consolidation embodying the invention. In this device are found pedicular screws 2 with nut 24 and damping means 25+26 as well as first claws 4 with nut 24 which are connected to plural rods 1, in this instance three in number 1a, 1b and 1c, via corresponding fasteners 3 and 3a, as well as a second vertebral claw 5 attached to the rod 1c.

The first and second rods 1a and 1b are two rods to be connected to screw assemblies respectively located to the right and left of the spinous apophysis of the spinal column and are therefore disposed substantially side by side by means of at least one of two transversal stabilizing means 6 and 7 embodying the invention.

The first and third rods 1a and 1c are disposed along the same side of the spinous apophysis, e.g. the right-hand side. The third rod 1c can be intended to extend a spinal consolidation already performed by the means connected to the first rod 1a; a longitudinal stabilizing means 8 embodying the invention is thus provided between the ends of the rods 1a and 1c.

Figure 7:
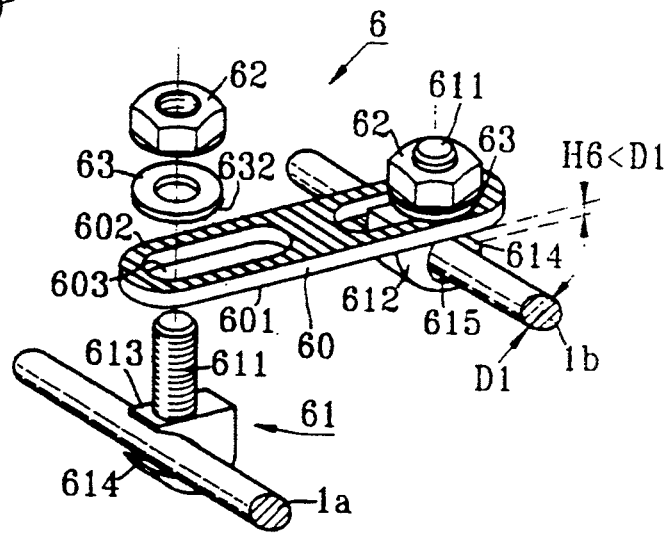
FIG. 7 is a partially exploded perspective view of a first transversal stabilizing means with a notched plate.

The first transversal stabilizing means 6 is shown in FIG. 7 and comprises a substantially rectangular extended stabilizing plate 60, two first rod hooks 61 and two nuts 62 and two notched washers 63.

The plate 60 has a smooth anterior side 601 to be applied against the two rods 1a and 1b and a posterior side 602 having parallel small indentations suitable for meshing with the notched sides 632 of the two washers 63. Two oblong slots 603 are provided longitudinally in the plate 60 in order to be disposed substantially transversely to the rods 1a and 1b. According to another embodiment, the two slots are replaced by a longer slot.

The hooks 61 are of shape similar to the first vertebral claws 4, such as the one shown in FIG. 4, but are of size reduced substantially by half compared with the claws 4. Thus, a hook 61 comprises a threaded section 611 and a circular semi-crescent-shaped holding portion 612 as well as a rectangular head 613 between the section 611 and the portion 612.

On the one hand, the length of the hook head 613 is substantially less than that of the slots 603 in the plate 60. On the other hand, the substantially semi-circular concave surface 615 of the hook 61 has a substantially smaller diameter than diameter D1 of the rods 1a, 1b and has a lateral opening 614 of which the parallel surfaces are substantially inclined in relation to the axis of the threaded section 611 and towards the section 611, and therefore in relation to the plate 60 subsequent to tightening. These two conditions enable a rod 1a, 1b accommodated in the bottom of the concave surface 615 of the hook to be pushed by a plate 60 of which a slot amply frames the head 613 without the rod 1a, 1b being able to escape from the hook 61. The distance H6 between the smooth surface 601 of the plate and the tip 614 of the hook is then less than the diameter D1 of the rod, as shown on the right-hand side in FIG. 7.

This rigid connection between the semi-crescent-shaped portion 612 of a hook 61 and a plate 60 is obtained:

(a) by hooking the corresponding rod 1a, 1b by the concave surface 615, (b) by slidably inserting the hook head 613 into a slot 603 of the plate, (c) by slipping a notched washer 602 onto the threaded section 611 protruding from the indented side 602 above the slot 603, (d) by meshing the notches of the notched washer 63 into the indentations of the side 602, and (e) finally, by screwing the nut 62 onto the section 611 so that the nut, along with the concave surface of the hook 615, hems in the washer 63, the plate 60 at the level of the slot 603, and the corresponding rod 1a, 1b.

Two first hooks 61 are thus mounted onto two rods 1a and 1b and connected together by a common plate 60. The hooks can be disposed back to back between the rods 1a and 1b as shown in FIG. 7, or face to face outside the two-rod assembly, or yet again in series and respectively outside and inside the two-rod assembly.

The two rods 1a and 1b can be stabilized by two plates 60 and four hooks 61 by forming a dimensionally stable quadrilateral so as to consolidate the assembly of these parts during contraction or relaxation as shown in FIG. 6. In this respect, the spacing at ends of the rods 1a and 1b can be increased or decreased, after loosening of the nuts 62 on the stabilizing plate 60 and removal of the notched washers 63 on the face of plate 602, by spreading apart or bringing closer the corresponding rod hooks and notched washers 61 and 63 by sliding of the hooks in the slots 603 of the plate 60.

Figure 8:
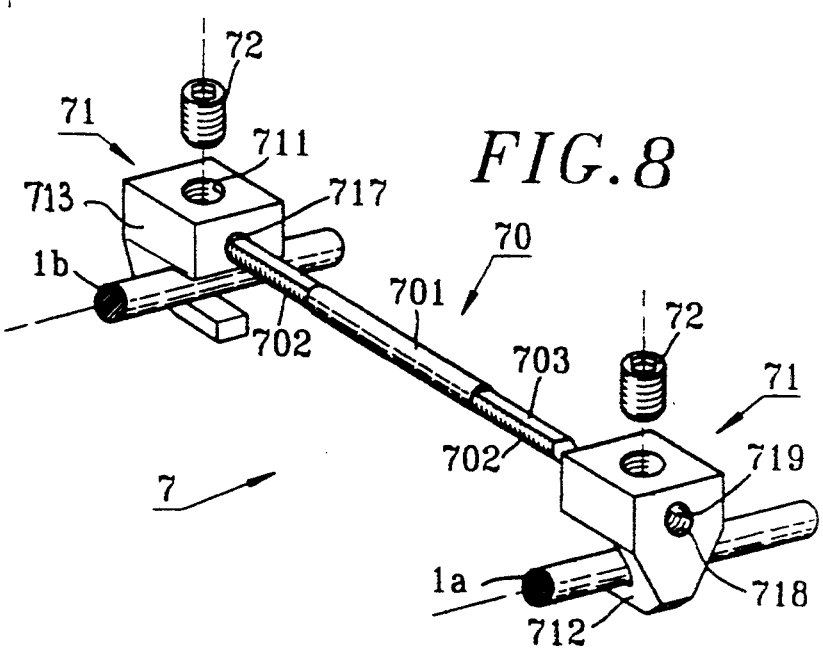
FIG. 8 is an exploded perspective view of a second transversal stabilizing means with a threaded bar.

A second transversal stabilizing means 7 comprises, in reference to FIG. 8, a thin bar 70 and two second rod hooks 71 each fitted with a small hexagonal socket headless locking screw 72.

The bar 70 comprises a smooth cylindrical central portion 701 separating two threaded end portions 702 which have coplanar longitudinal flat surfaces 703 parallel to the axis of the bar 70.

Each of the second rod hooks 71 is of shape similar to a second vertebral claw 5, such as the one shown in FIG. 5, but of size reduced substantially by half. A hook 71 thus comprises a parallelepiped head 713 and a substantially circular semi-crescent-shaped hooking portion 712 for hooking a rod 1a, 1b. The head 713 comprises a half-tapped oblong hole 717 which extends parallel to the hooked hooking portion 712 and perpendicular to the rod 1a, 1b hooked by the latter. Perpendicular to the posterior side of the head 713 and in the axial extension of an oblong section of the hole 717, a tapped hole 711 is provided to engage with a locking screw 72 perpendicular to both the bar 70 and the rod 1a, 1b subsequent to assembly.

The hole 717 is divided, in the transversal section, into a first concave longitudinal portion at least partially tapped 718 and a second smooth concave longitudinal portion 719 in relation to a plane parallel to the axis of hole 717 and perpendicular to hole 711. The oblong section of the hole 718 is longer and at least substantially as wide as the diameter of the threaded bar portions 702. The first portion 718 is preferably tapped at least on the bottom with a threading corresponding to the threaded portions 702 of the bar 70 and is disposed opposite the tapped hole 711 in relation to the axis of hole 717, towards the semi-crescent-shaped anterior portion 712. The second smooth portion 719 is disposed towards the posterior side of the hole 717, and the tapped hole 711 opens transversely into this smooth portion.

The second stabilizing means 7 is mounted as follows.

Each of the second hooks 71, of which the semi-tapped oblong holes 717 have been cleared of the screws 72, are slid onto the threaded end portions 702 of the bar 70 on both sides of the two rods 1a and 1b and are disposed with their circular semi-crescent-shaped portions 712 e.g. opposite one another as shown in FIG. 8. After hooking of the rods 1a and 1b by the hooking portions 712 to attempt to bring them closer together according to FIG. 8, or to spread them apart according to other embodiments previously mentioned for the hooks 61, the threaded bar portions 702 are meshed into the tapped portions 718 of the holes 717. These meshings are maintained by screwing into the holes 711 the screws 72 of which the flat ends push the flat surfaces 703 against the tapped portions 718. Under these conditions, the bar 70 is stopped both as regards rotation by means of the pressure of the screws 72 exerted on the flat surfaces 703, and as regards axial translation by means of the self-locking meshing of the threading of the bar portions 702 into the threading of the half-tapped hole portions 718.

This assembly is highly resistant against all spacing or spreading of the hooks 71 due to the relatively high number of threads cooperating between the hole portions 718 and the bar portions 702. Furthermore, this assembly is quickly mounted or dismounted, without requiring a long unscrewing of the bar ends 702 as the latter are placed in the oblong holes 718.

Figure 9:
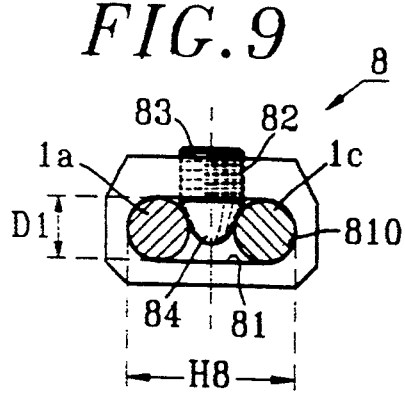
FIG. 9 is a transversal view at the end of a longitudinal stabilization connector for two consolidation rods.

As shown in FIGS. 6 and 9, the longitudinal stabilizing means is in the form of a rod connector 8. This connector 8 has a parallelepiped shape in which is provided a longitudinal orifice 81 with an oblong cross-section. The width of the orifice 81 and the diameter of the semi-circular end walls 810 of the orifice 81 are substantially equal to the diameter D1 of the rods 1a, 1c. The posterior side of the connector 8 is drilled with a tapped hole 82 opening transversely and centrally into the oblong orifice 81. The hole 82 is suitable for receiving a small hexagonal socket headless binding screw 83 having a tapered smooth pointed end 84.

The height H8 (transversal length) of the orifice 81 is greater than the sum of the diameters of the rods 1a and 1c, but less than the sum of the diameters of the rods 1a and 1c and of the binding screw 83. Under these conditions, after having slid the ends of the two rods 1a and 1c into the oblong orifice 81, the binding screw 83 is screwed into the orifice 82 in order for its tapered pointed end 84 to gradually space apart the rods 1a and 1c and to firmly wedge them against the semi-circular walls 810 facing the hole 81, which definitively and solidly connects the two rods 1a and 1c.

According to other embodiments, a connector has an orifice 81 of greater height in order to connect plural rods thereto side by side by wedging. For instance, said height H8 is greater than the sum of the diameters of three, respectively four consolidation rods and less than the sum of the diameters of the three, respectively four rods plus the diameters of two, respectively three binding screws screwed transversely into the connector and each having a tapered end disposed between two respective rods.

What we claim is:

1. An osteosynthesis device comprising
a rod, a member having a threaded section extending from a head and fitted with a nut, and a connecting fastener,
said fastener comprising a first smooth bore passed through by said rod, a first slit opening axially into said first bore, and a second smooth bore substantially perpendicular to said first slit and passed through by a portion of said threaded member section located between said member head and said nut, and a second slit opening axially into said second bore and having a width greater than the diameter of said threaded member section.

2. The device claimed in claim 1, wherein the nut comprises a cylindrical shank having a diameter that is substantially equal to the diameter of said second bore and more than the width of said second slit thereby penetrating into said second bore.

3. The device claimed in claim 2, wherein said second slit extends substantially perpendicular to said first bore.

4. The device claimed in claim 2, wherein said second slit extends substantially parallel to said first bore.

5. The device claimed in claim 1, wherein said fastener comprises a locking means radial to said first bore in order to temporarily maintain said fastener motionless on said rod.

6. A device as claimed in claim 1, comprising a means passed through by said threaded section and located between said member head and said nut for damping relative movements between said rod and said member.

7. The device claimed in claim 6, wherein said damping means comprises a washer made of damping material, said washer being in contact with at least one metal washer.

8. The device claimed in claim 1, wherein said member comprises a portion which is at least partially threaded and separated from said threaded section by said head.

9. The device claimed in claim 1, wherein said member comprises a claw-shaped portion separated from said threaded section by said head.

10. A device as claimed in claim 1, comprising a means having a bore slidably passed through by said rod and having a claw-shaped portion, and a locking means radial to said rod for maintaining motionless said means slidably passed through by said rod.

11. A device as claimed in claim 1, comprising a second rod disposed laterally to the previously mentioned first rod, and a transversal stabilizing means connecting said first and second rods.

12. A device as claimed in claim 1, comprising a second rod substantially parallel to the previously mentioned first rod, and a longitudinal stabilizing means connecting ends of said first and second rods.

13. An osteosynthesis device comprising:
two rods,
plural members each having a threaded section extending from a head and fitted with a nut,
plural connecting fasteners,
each of said fasteners comprising a first bore passed through by one of said two rods, a first slit opening axially into said first bore, and a second bore substantially perpendicular to said first slit and passed through by a portion of said threaded section of one of said plural members located between said head of and said nut on said one of said plural members, and a second slit opening axially into said second bore and having a width greater than the diameter of said threaded section,
a plate extending transversal to said two rods and having a longitudinal slot,
two hooks each having a threaded section passing through said plate slot and a holding portion partially surrounding one of said two rods, and
two nuts respectively screwed onto threaded hook sections for tightening said plate against said two rods thereby confining said rods between said plate and said hook holding portions.

14. The device as claimed in claim 13, wherein said holding portion of each hook is located into said plate slot and has an opening substantially inclined in relation to and towards said threaded section of said hook.

15. The device as claimed in claim 13 wherein one of sides of said plate is indented thereby cooperating with notched washers slid over said threaded sections of said hooks.

16. An osteosynthesis device comprising
two rods,
plural members each having a threaded section extending from a head and fitted with a nut,
plural connecting fasteners,
each of said fasteners comprising a first bore passed through by one of said two rods, a first slit opening axially into said first bore, and a second bore substantially perpendicular to said first slit and passed through by a portion of said threaded section of one of said plural members located between said head of and said nut on said one of said plural members, and a second slit opening axially into said second bore and having a width greater than the diameter of said threaded member section,
a bar extending transversal to said two rods,
two hooks having hooking portions to be hooked to said two rods, and
means for quickly securing said hooks to ends of said bar.

17. An osteosynthesis device comprising
two rods,
plural members each having a threaded section extending from a head and fitted with a nut,
plural connecting fasteners,
each of said fasteners comprising a first bore passed through by one of said two rods, a first slit opening axially into said first bore, and a second bore substantially perpendicular to said first slit and passed through by a portion of said threaded section of one of said plural members located between said head of and said nut on said one of said plural members, and a second slit opening axially into said second bore and having a width greater than the diameter of said threaded member section,
a bar extending transversal to said two rods and having ends which each comprise a longitudinal tapped portion and a longitudinal flat surface, and
two hooks each having a hooking portion to be hooked to one of said two rods and an oblong hole for free receiving one of the bar ends,
said hole having a tapped longitudinal portion for meshing with said tapped portion of said one of said bar ends, and a smooth portion into which opens a tapped hole containing a locking screw pressed against said flat surface of said one of said ends.

18. An osteosynthesis device comprising
two rods substantially parallel,
plural members each having a threaded section extending from a head and fitted with a nut,
plural connecting fasteners,
each of said fasteners comprising a first bore passed through by one of said two rods, a first slit opening axially into said first bore, and a second bore substantially perpendicular to said first slit and passed through by a portion of said threaded section of one of said plural members located between said head of and said nut on said one of said plural members, and a second slit opening axially into said second bore and having a width greater than the diameter of said threaded section,
a connector having a longitudinal orifice with an oblong cross-section passed through by said two rods, and
a means for spacing apart said two rods thereby blocking said rods in said orifice.

19. The device as claimed in claim 18, wherein said spacing means comprises a screw having a pointed end which opens transversely into said orifice of said connector and between said two rods and wedges said tow rods against walls facing the hole.

20. An osteosynthesis device, comprising
plural rods,
plural members each having a threaded section extending from a head and fitted with a nut,
plural connecting fasteners,
each of said fasteners comprising a first bore passed through by one of said two rods, a first slit opening axially into said first bore, and a second bore substantially perpendicular to said first slit and passed through by a portion of said threaded section of one of said plural members located between said head of and said nut on said one of said plural members, and a second slit opening axially into said second bore and having a width greater than the diameter of said threaded section,
a connector having a longitudinal orifice with an oblong cross-section passed through by said rods, and
plural means fewer by one unit in number than said rods for each spacing apart respective two of said plural rods thereby blocking said plural rods in said orifice.

* * * * *